(12) United States Patent
Lack et al.

(10) Patent No.: US 11,957,302 B2
(45) Date of Patent: Apr. 16, 2024

(54) USER-INTERFACE FOR VISUALIZATION OF ENDOSCOPY PROCEDURES

(71) Applicant: Verily Life Sciences LLC, South San Francisco, CA (US)

(72) Inventors: Erik Lack, San Francisco, CA (US); Roman Goldenberg, Haifa (IL); Daniel Freedman, Haifa (IL); Ehud Rivlin, Haifa (IL)

(73) Assignee: Verily Life Sciences LLC, South San Francisco, CA (US)

( * ) Notice: Subject to any disclaimer, the term of this patent is extended or adjusted under 35 U.S.C. 154(b) by 49 days.

(21) Appl. No.: 17/499,748

(22) Filed: Oct. 12, 2021

(65) Prior Publication Data

US 2022/0369899 A1 Nov. 24, 2022

Related U.S. Application Data

(60) Provisional application No. 63/192,479, filed on May 24, 2021.

(51) Int. Cl.
*A61B 1/00* (2006.01)
*A61B 1/31* (2006.01)
(Continued)

(52) U.S. Cl.
CPC .......... *A61B 1/0004* (2022.02); *A61B 1/0005* (2013.01); *A61B 1/31* (2013.01);
(Continued)

(58) Field of Classification Search
CPC . A61B 1/00009; A61B 1/0004; A61B 1/0005; A61B 1/00147; A61B 1/00174;
(Continued)

(56) References Cited

U.S. PATENT DOCUMENTS

| 8,248,413 B2 | 8/2012 | Gattani et al. | |
| 2011/0032347 A1* | 2/2011 | Lacey | G06T 7/0012 348/E7.085 |

(Continued)

FOREIGN PATENT DOCUMENTS

| EP | 3366191 A1 * | 8/2018 | ......... A61B 1/00006 |
| EP | 3666159 A1 * | 6/2020 | ......... A61B 1/00004 |

(Continued)

OTHER PUBLICATIONS

Extended European Search Report, dated Oct. 17, 2022, in corresponding European Patent Application No. 22173462.7-1126, 7 pages.

(Continued)

*Primary Examiner* — Behrooz M Senfi
(74) *Attorney, Agent, or Firm* — CHRISTENSEN O'CONNOR JOHNSON KINDNESS PLLC

(57) ABSTRACT

A user-interface for visualizing a colonoscopy procedure includes a video region and a navigational map upon which coverage annotations are displayed. A live video feed received from a colonoscope is displayed in the video region. The navigational map depicts longitudinal sections of a colon. The coverage annotations are presented on the navigation map and indicate whether one or more of the longitudinal sections is deemed adequately inspected or inadequately inspected during the colonoscopy procedure.

22 Claims, 11 Drawing Sheets

(51) Int. Cl.
    *A61B 90/00*    (2016.01)
    *G06T 7/00*    (2017.01)
(52) U.S. Cl.
    CPC ............ *A61B 90/39* (2016.02); *G06T 7/0012*
            (2013.01); *G06T 2207/10068* (2013.01); *G06T*
                *2207/20081* (2013.01); *G06T 2207/30032*
                                                (2013.01)
(58) Field of Classification Search
    CPC ........... A61B 1/31; A61B 34/20; A61B 90/39;
            G06T 2207/10068; G06T 2207/20081;
                G06T 2207/30032; G06T 7/0012
    USPC .......................................................... 348/77
    See application file for complete search history.

(56) References Cited

U.S. PATENT DOCUMENTS

| | | | | |
|---|---|---|---|---|
| 2018/0279852 | A1* | 10/2018 | Rafii-Tari | A61B 10/04 |
| 2019/0090728 | A1 | 3/2019 | Fanenbruck et al. | |
| 2019/0191173 | A1 | 6/2019 | Wade | |
| 2021/0378484 | A1* | 12/2021 | Ninh | G16H 15/00 |

FOREIGN PATENT DOCUMENTS

| | | | | |
|---|---|---|---|---|
| EP | 3666160 | A1 * | 6/2020 | ......... A61B 1/00009 |
| JP | 2005-512693 | | 5/2005 | |
| JP | 2013-200590 | | 10/2013 | |
| JP | 2018139847 | A | 9/2018 | |
| WO | 2003/053505 | | 7/2003 | |
| WO | 2009128055 | A1 | 10/2009 | |
| WO | 2016004007 | A1 | 1/2016 | |
| WO | 2017042812 | A2 | 3/2017 | |
| WO | 2020242949 | A1 | 12/2020 | |
| WO | 2020245815 | A1 | 12/2020 | |
| WO | 2021011190 | A1 | 1/2021 | |
| WO | 2021048326 | A1 | 3/2021 | |

OTHER PUBLICATIONS

Office Action, dated Jun. 9, 2023, in corresponding Japanese Patent Application No. 2022-082605, 5 pages. (English translation not available).

Freedman, et al., Detecting Deficient Coverage in Colonoscopies, IEEE Transactions on Medical Imaging, Jan. 23, 2020. 10 pages.

Freedman et al., Detecting Deficient Coverage in Colonoscopies, arXiv:2001.08589v3 [cs.CV] Mar. 29, 2020, 12 pages.

Ma et al., Real-Time 3D Reconstruction of Colonoscopic Surfaces for Determining Missing Regions, Advances in Intelligent Data Analysis, XIX, Oct. 10, 2019, 10 pages.

Freedman et al., Detecting Deficient Coverage in Colonoscopies, IEEE Transactions on Medical Imaging, vol. 39, No. 11, Nov. 2020, 12 pages.

Freedman et al., Using Machine Learning to Detect Deficient Coverage in Colonoscopy Screenings, Google AI Blog, Aug. 28, 2020, 4 pages.

Endoscope Leap Forward in Endoscope Technology, Sep. 23, 2021 date downloaded from web https://www.aurishealth.com/monarch-platform, 7 pages.

SCOPEPILOT—The Next Generation 3D colon navigation system, Pentax Medical, May 24, 2021, date downloaded from web https://www.pentaxmedical.com/pentax/en/95/2/SCOPEPILOT-The-next-generation-3D-colon-navigation-system, 7 pages.

Endoscopic Access to Peripheral Nodules, Access Deeper into the Lung Periphery, Sep. 23, 2021 date downloaded from web https://www.aurishealth.com/procedure/bronchoscopy/features, 11 pages.

Office Action, dated Nov. 17, 2023, in corresponding Japanese Patent Application No. 2022-082605, 4 pages. (English translation not available).

\* cited by examiner

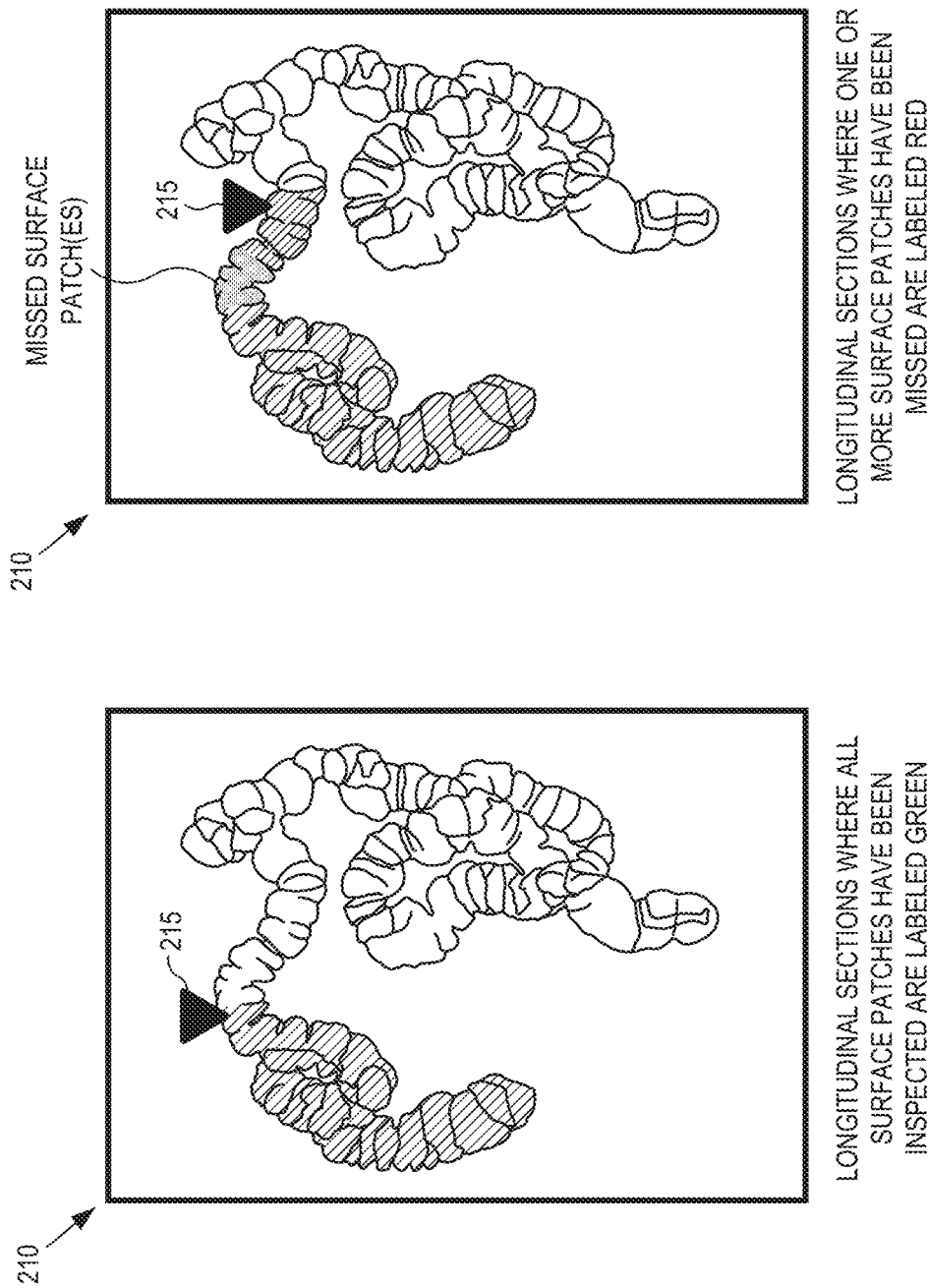

USER-INTERFACE FOR VISUALIZATION OF ENDOSCOPY PROCEDURES

CROSS-REFERENCE TO RELATED APPLICATIONS

This application claims the benefit of U.S. Application No. 63/192,479, filed on May 24, 2021, the contents of which are incorporated herein by reference.

TECHNICAL FIELD

This disclosure relates generally to endoscopy, and in particular, but not exclusively, to user-interfaces to aid colonoscopy.

BACKGROUND INFORMATION

When an endoscopist performs a colonoscopy, one of the most important tasks during the withdrawal phase is to ensure that they have visualized every surface of the colon in order to detect all the polyps. 20% to 24% of polyps that have the potential to become cancerous (adenomas) are missed. Two major factors that may cause an endoscopist to miss a polyp are: (1) the polyp appears in the field of view, but the endoscopist misses it, perhaps due to its small size or flat shape; and (2) the polyp does not appear in the field of view, as the endoscopist has not fully covered the relevant area during the procedure.

Conventional products that assist clinicians/endoscopists with detecting polyps do not currently support features for coverage visualization.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
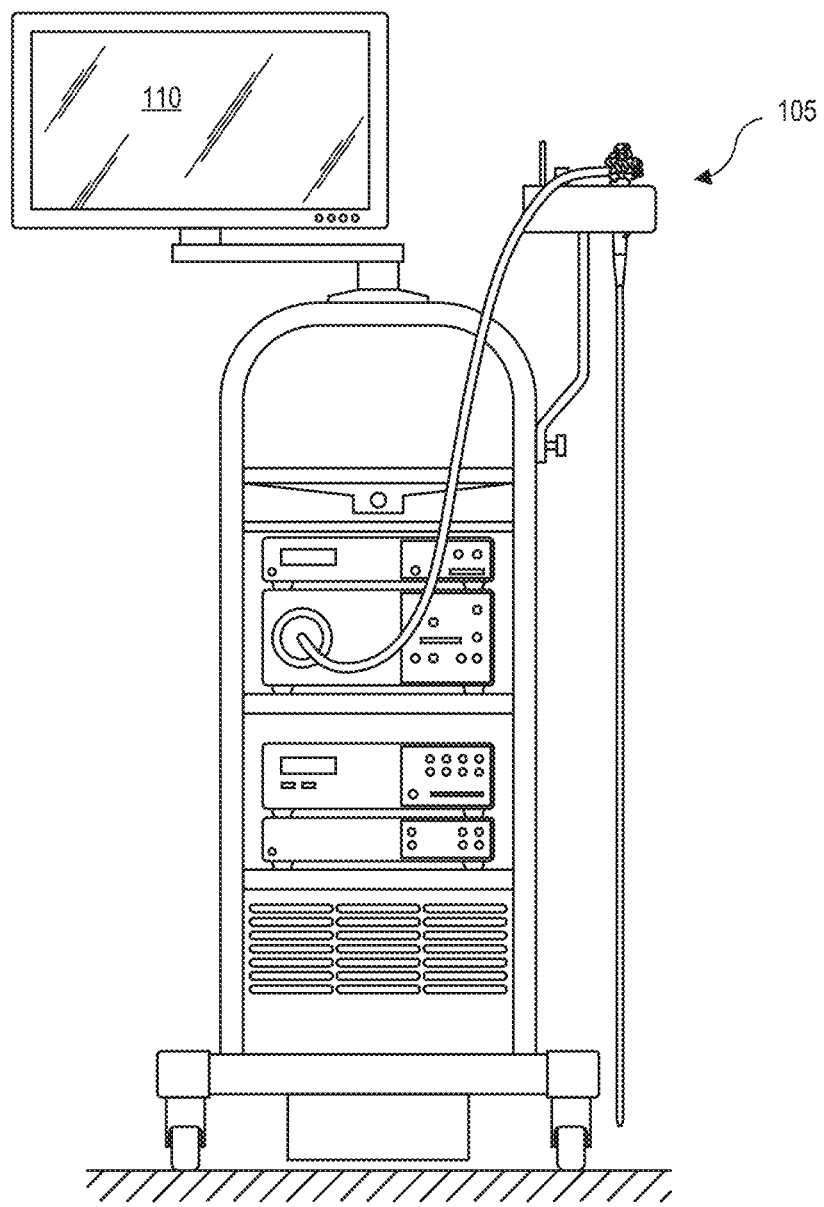
FIG. 1A illustrates a colonoscopy tower system, in accordance with an embodiment of the disclosure.

Embodiments of a system, apparatus, and method for a user-interface (UI) to aid visualization of an endoscopy (particularly colonoscopy) procedure are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Conventional endoscopy and colonoscopy interfaces only display the live video feed on the screen without providing any other user aids. Embodiments of the colonoscopy user-interface (UI) described herein introduce additional on-screen elements to support and aid the endoscopist fully visualize every surface patch of a colon to improve polyp detection and the reliability of the overall colonoscopy procedure. In certain embodiments, machine learning (ML) models may be used to track relative position, depth, and angle of the colonoscope camera within the colon. Examples of these image analysis techniques are described in "Detecting Deficient Coverage in Colonoscopies," Freedman et al., IEEE Transactions On Medical Imaging, Vol. 39, No. 11, November 2020. ML models may further be trained to provide polyp detection and/or optical biopsies. Position, depth, and angle tracking along with feature detection (polyp detection) and optical biopsy may all be performed based upon image analysis of the video output from the colon. In other embodiments, additional position sensors or real-time scanning techniques may be implemented to obtain position/depth tracking information of the distal end of the colonoscope.

The data obtained from the above image analysis of a live video feed from a colonoscope may be leveraged to display a number of beneficial on-screen visual aids in a colonoscopy UI. These visual aids provide improved operator context and visualization of the colonoscopy procedure. For example, these aids may include a navigational map that depicts longitudinal sections of a colon, a position marker indicating a position of a field of view (FOV) of a camera capturing the live video feed, annotations indicating inspection status of different longitudinal sections of a colon, a cross-sectional coverage map indicating whether portions or surface patches of a longitudinal section have been adequately inspected, guidance arrows prompting the endoscopist back to a longitudinal section deemed inadequately inspected, annotations highlighting detected polyps, and display of a variety of other valuable feedback data (e.g., estimated withdrawal time, polyp detected status, polyp detected history, important notifications, etc.). It should be appreciated that the terms "annotate" or "annotation" are broadly defined herein to include both textual markups (e.g., on screen textual prompts or dialog) and graphical/pictorial markups (e.g., on screen boxes, arrows, shading, coloring, highlighting, etc.).

Providing these visual aids on the colonoscopy UI in real-time and contemporaneously alongside the live video feed from the colonoscope provides a higher level of context and orientation to the endoscopist. The visual aids increase confidence that all surface patches of the colon (i.e., the internal surfaces of the colon) have been reviewed or provide actionable, real-time feedback to guide the endoscopist back to a missed surface patch. Ultimately, the visual aids improve the operator experience thus providing improved detection of polyps and improved confidence in the overall colonoscopy procedure.

Figure 1B:
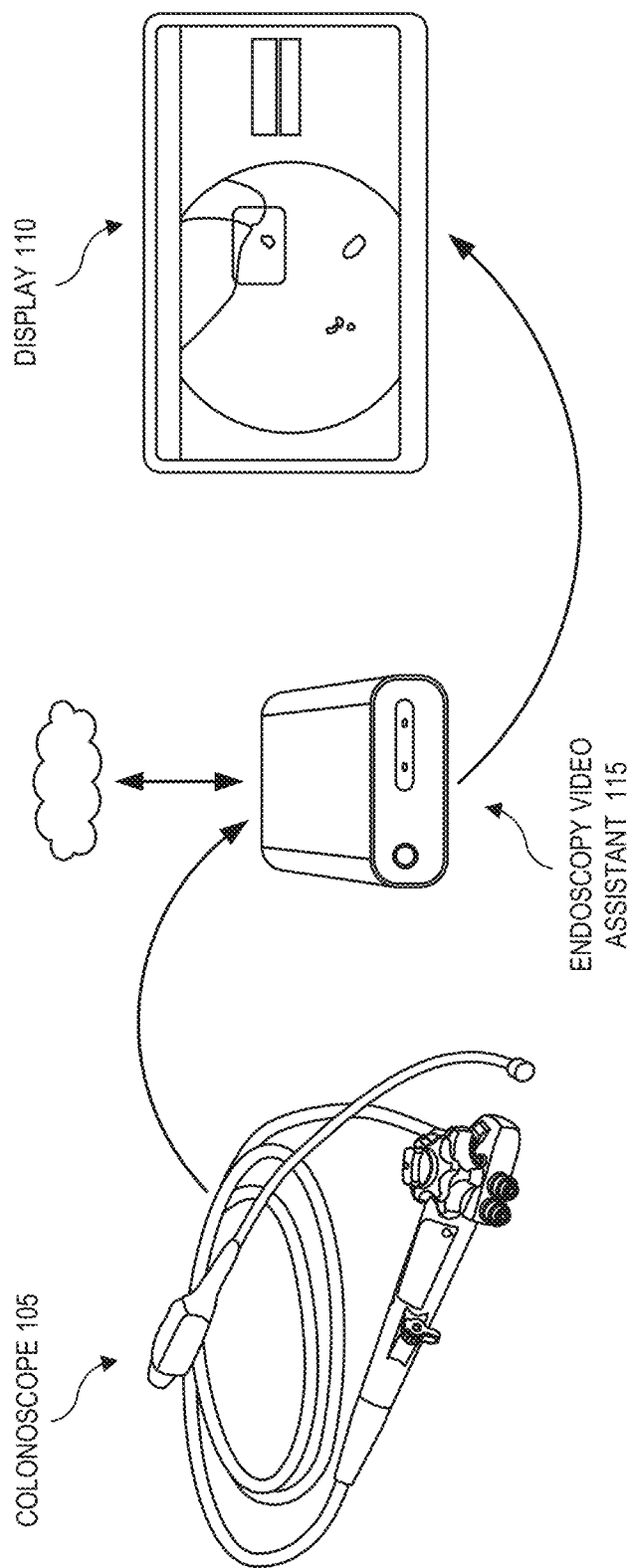
FIG. 1B illustrates an endoscopy video assistant capable of generating a colonoscopy user-interface including a live video feed and various visual aids during a colonoscopy procedure, in accordance with an embodiment of the disclosure.

FIG. 1A illustrates a colonoscopy tower system 100, in accordance with an embodiment of the disclosure. System 100 illustrates an example hardware system in which embodiments of the improved colonoscopy UI described herein may be used. System 100 includes an endoscope or colonoscope 105 coupled to a display 110 for capturing images of a colon and displaying a live video feed of the colonoscopy procedure. In one embodiment, the image analysis and UI overlays described herein may be performed and generated by a processing box that plugs in between the colonoscope 105 and display 110. FIG. 1B illustrates an example endoscopy video assistant (EVA) 115 capable of generating the colonoscopy UI described herein. EVA 115 may include the necessary processing hardware and software, including ML models, to perform the real-time image processing and UI overlays. For example, EVA 115 may include a data storage, a general-purpose processor, graphics processor, and video input/output (I/O) interfaces to receive a live video feed from colonoscope 105 and output the live video feed within a UI that overlays various visual aids and data. In some embodiments, EVA 115 may further include a network connection for offloading some of the image processing and/or reporting and saving coverage data for individual patient recall and/or longitudinal, anonymized studies. The colonoscopy UI may include the live video feed reformatted, parsed, or scaled into a video region (e.g., video region 205 in FIG. 2), or may be a UI overlay on top of the existing colonoscopy monitor feed to maintain the original format, resolution, and integrity of the colonoscopy live video feed as well as reduce any latency.

Figure 2:
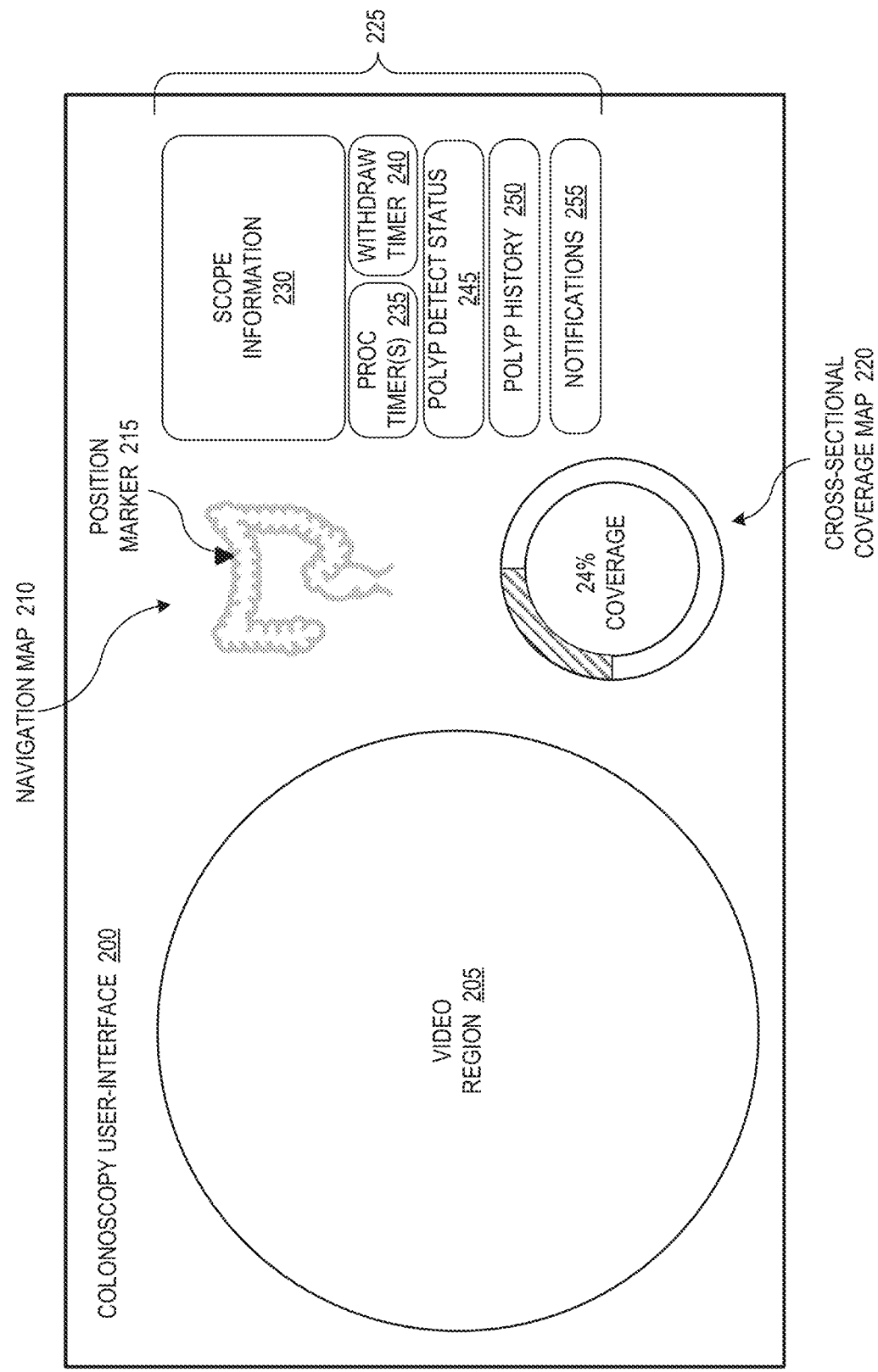
FIG. 2 illustrates a colonoscopy user-interface for visualizing a colonoscopy procedure, in accordance with an embodiment of the disclosure.

FIG. 2 illustrates a colonoscopy UI 200 for visualizing a colonoscopy procedure, in accordance with an embodiment of the disclosure. The illustrated embodiment of colonoscopy UI 200 includes a video region 205 for displaying a live video feed, a navigation map 210 with a position marker 215, a cross-sectional coverage map 220, and a region for procedure data 225. The illustrated embodiment of procedure data 225 includes scope information 230, procedure timer(s) 235, withdrawal timer 240, polyp detected status 245, polyp detected history 250, and notifications 255.

As mentioned, video region 205 provides a region within colonoscopy UI 200 to display a live video feed of the interior of a colon captured during a colonoscopy procedure by a camera of colonoscope 105. In other words, video region 205 may be used to display the real-time FOV captured by the camera of colonoscope 105. Although video region 205 is illustrated as having a round FOV, in other embodiments, the FOV may be rectangular, square, or otherwise.

Navigation map 210 depicts longitudinal sections of the colon. Each longitudinal section represents a different depth into the colon (or large intestine) extending from the rectum or anal canal to the cecum. Navigation map 210 may be implemented as an anatomical atlas or caricature being representative of the colon, or an actual three-dimensional (3D) model of the colon. In the case of a 3D model, the 3D model of the colon may be generated during an insertion phase of the colonoscopy procedure as colonoscope 105 is inserted into the anal canal and moved towards the cecum. The live video feed during insertion may be analyzed and mapped into the 3D model. In the illustrated embodiment, navigation map 210 is annotated with position marker 215 to indicate a position of the FOV of the live video feed and by extension the distal end of colonoscope 105 within the colon. In one embodiment, position marker 215 does not appear on navigation map 210 until after the colon has been fully mapped or traversed during the insertion phase. After the insertion phase, position marker 215 moves in real-time tracking the position of the distal end of colonoscope 105 and the FOV of the live video feed during the withdrawal phase.

Figures 3A, 3B:
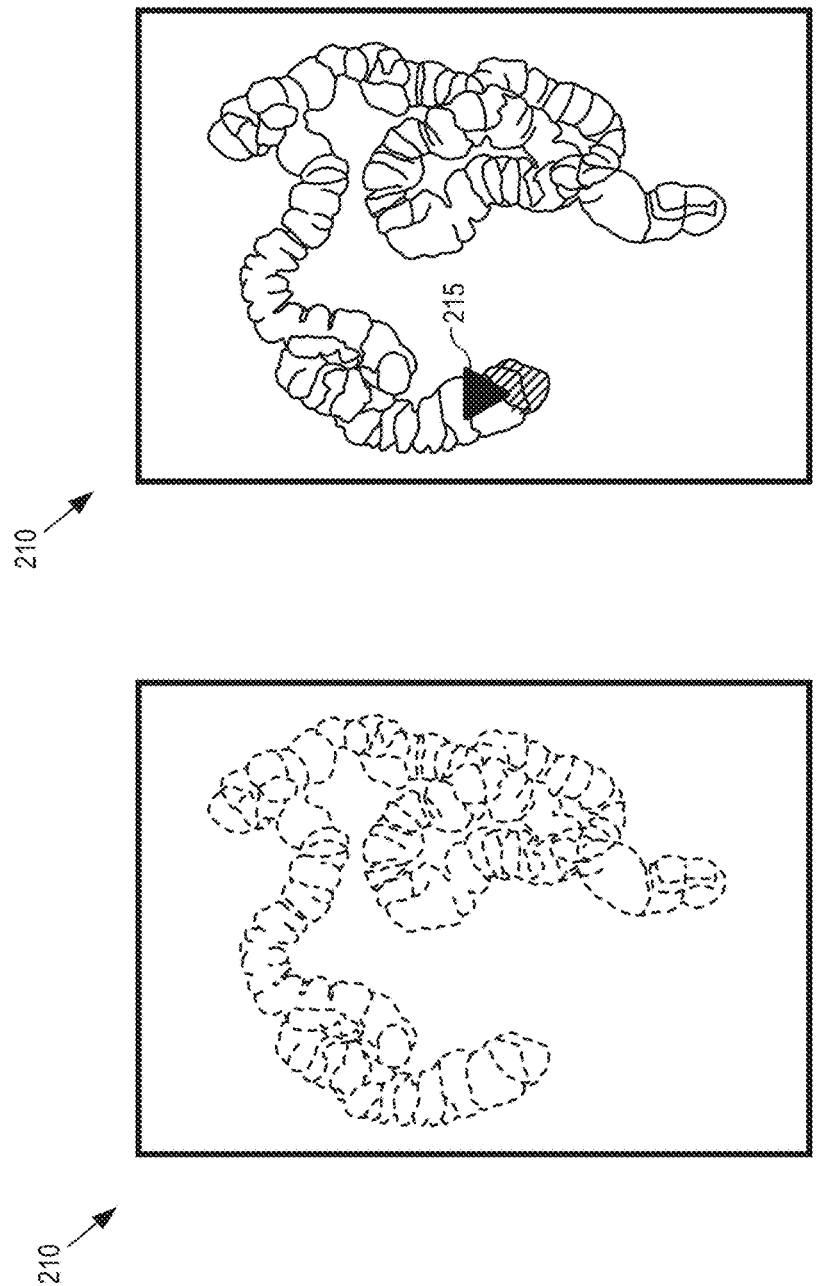
FIGS. 3A, B, C, and D illustrate a navigational map of a colon with coverage annotations and a position marker to aid a colonoscopy procedure, in accordance with an embodiment of the disclosure.

FIGS. 3A-D illustrate further details of navigational map 210, in accordance with an embodiment of the disclosure. As illustrated in FIG. 3A, navigational map 210 may be initially presented in a lighter shade or grayed out shade during the insertion phase of the colonoscopy procedure. In yet other embodiments, navigational map 210 may not be initially presented until the end of the insertion phase or beginning of the withdrawal phase. The insertion phase may be deemed complete once the cecum is reached and recognized as the end of the colon. The colon illustration may be withheld, grayed out, or presented in a lighter shade while the colon is being spatially mapped during the insertion phase. The spatial mapping may be achieved using a 3D visual mapping via image analysis of the live video feed during the insertion phase. In other embodiments, additional sensors and/or tracking devices may be used (alone or in conjunction with the image analysis) to facilitate spatial mapping or generation of a full 3D model of the colon. For example, ultrasound imaging, magnetic tracking, etc. may be used to track the distal tip of colonoscope 105 as it progresses through the colon.

In FIG. 3B, upon commencement of the withdrawal phase, navigation map 210 is fully presented and position marker 215 displayed. Navigation map 210 along with position marker 215 present the endoscopist with a visual representation of the position of the FOV of the live video feed within the colon along with a visual estimation of the remaining distance to traverse during the withdrawal phase.

Referring to FIGS. 3C and 3D, as colonoscope 105 is withdrawn through the colon, navigation map 210 is annotated to illustrate the inspection status of each longitudinal section along the way. This annotation may be updated in real-time during the withdrawal phase. Longitudinal sections deemed fully inspected (i.e., all surface patches in those longitudinal sections have been adequately inspected) are annotated as such. For example, longitudinal sections that are deemed adequately inspected may be colored green (FIG. 3C). Correspondingly, if the endoscopist withdrawals through a given longitudinal section without fully inspecting every surface patch within that longitudinal section, then the corresponding longitudinal section on navigation map 210 is annotated to represent an inadequate inspection. For example, the inadequately inspected section may be colored red (FIG. 3D) to indicate that one or more surface patches of the colon in the longitudinal section has been deemed inadequately inspected. Of course, other colors, shades, or labels may be used to indicate adequate or inadequate inspection of a given longitudinal section.

Figure 4:
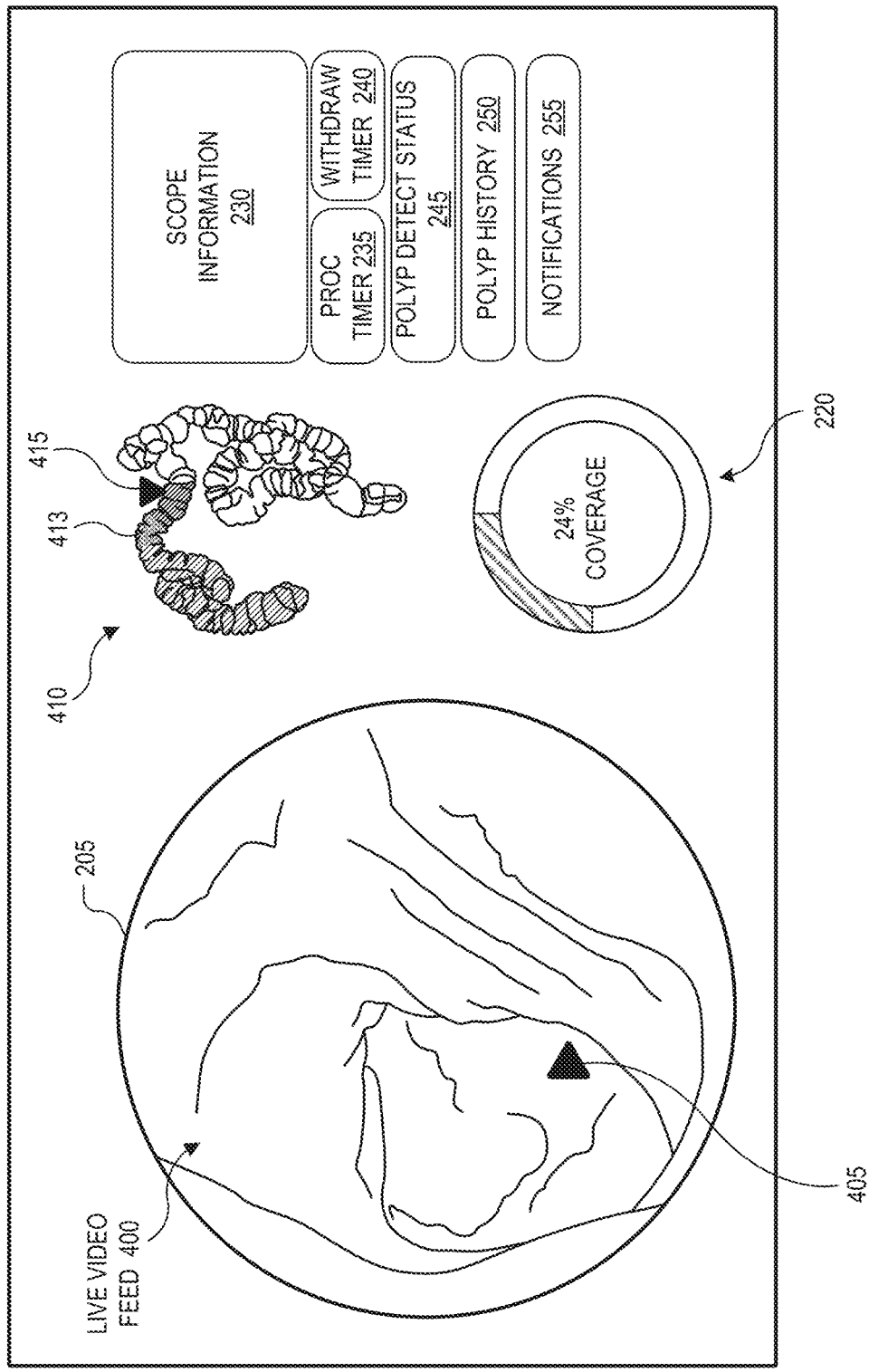
FIG. 4 illustrates a guidance arrow overlaying the live video feed guiding an operator of the colonoscope back to one of the longitudinal sections of the colon deemed inadequately inspected, in accordance with an embodiment of the disclosure.

FIG. 4 illustrates a guidance arrow 405 overlaying a live video feed 400 guiding an operator (endoscopist) of colonoscope 105 back to one of the longitudinal sections of the colon deemed inadequately inspected. As illustrated, navigational map 410 is annotated to depict that a longitudinal section 413 is deemed inadequately inspected. Since the distal end of colonoscope 105 has been withdrawn past longitudinal section 413 (see position marker 415), guidance arrow 405 may be overlaid on live video feed 400 within video region 205 to visually guide the endoscopist back to longitudinal section 413. Guidance arrow 405 can help the endoscopist navigate the twist, turns, and folded anatomical structures of the colon to return to longitudinal section 413 for a more thorough inspection of the missed surface patches.

Figure 5:
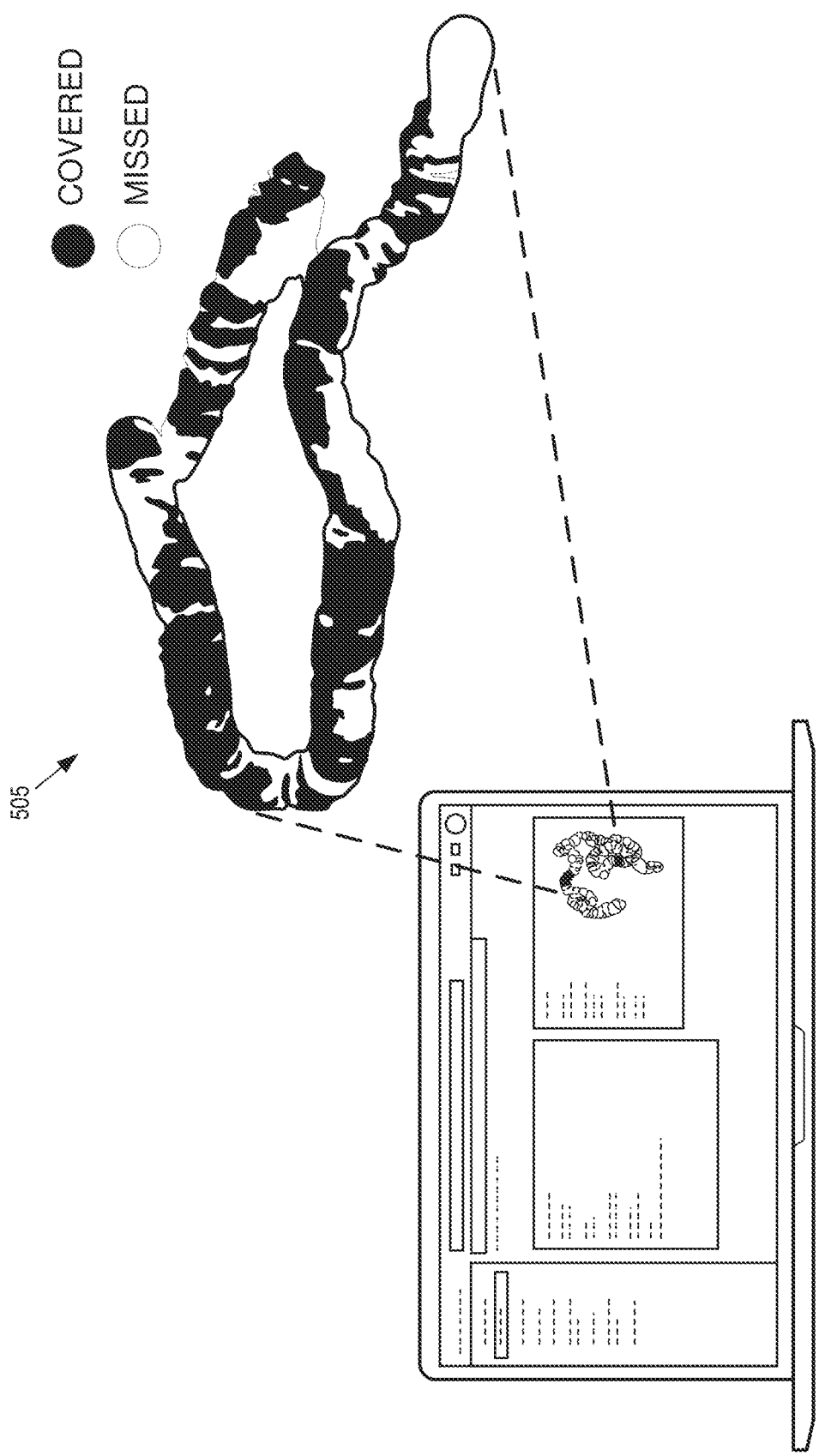
FIG. 5 illustrates coverage data collected from a multitude of colonoscopy procedures, in accordance with an embodiment of the disclosure.

The data of adequately vs inadequately inspected longitudinal sections and/or surface patches may be anonymized by EVA 115 and uploaded to a server or cloud-based service to collect coverage data from a multitude of colonoscopy procedures. As illustrated in FIG. 5, a coverage map 505 may be generated based upon many colonoscopies to instruct practitioners in the field, which surface patches of a colon are more likely to be missed than others, where polyps are commonly found, etc. This feedback data may also be correlated with anonymized demographic data including age, race, sex, etc. to provide further insights and improve the success, reliability, and confidence in colonoscopy procedures.

Returning to FIG. 2, the illustrated embodiment of colonoscopy UI 200 further includes a cross-sectional coverage map 220. Cross-sectional coverage map 220 indicates whether angular portions of a cross-section of a given longitudinal section of the colon is deemed adequately or inadequately inspected. For example, cross-section coverage map 220 may display a cross-sectional map of the current longitudinal section indicated by position marker 215. In the illustrated embodiment, cross-sectional coverage map 220 is indicating that only the surface patch of the colon residing in the upper left quadrant of the current longitudinal section has been adequately inspected and the remaining 76% of the perimeter surface patches of the current longitudinal section have not yet been adequately inspected. During the insertion phase, the image inspection software (e.g., trained neural networks) maps and orients itself to the colon. During the withdrawal phase, cross-sectional coverage map 220 may map surface patch inspection status relative to the frame of reference of the FOV of the camera during the insertion phase. In other embodiments, cross-sectional coverage map 220 maps surface patch inspections relative to a current frame of reference or other anatomical reference frames (e.g., sagittal, coronal, or median planes).

Figure 6:
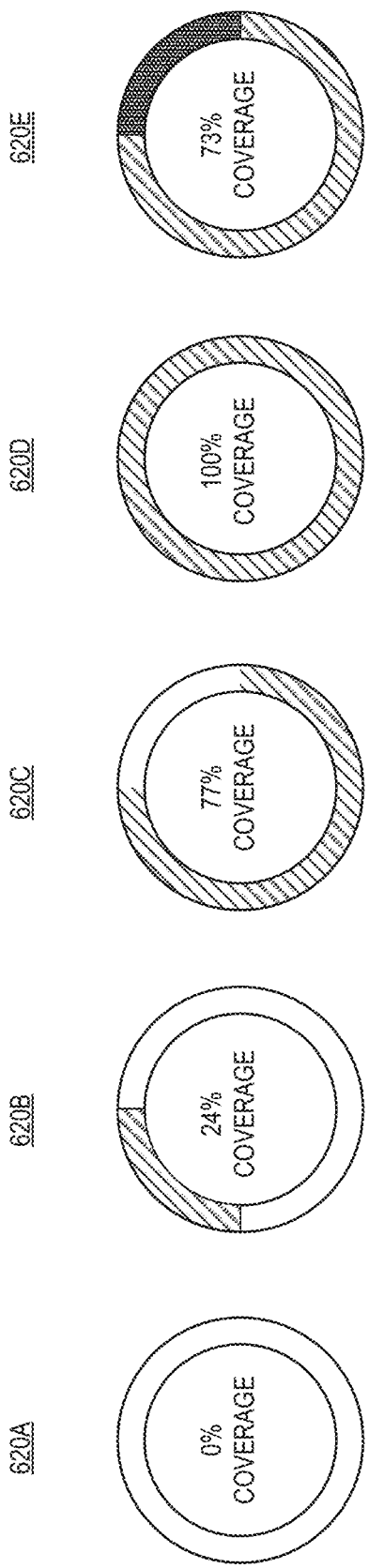
FIG. 6 illustrates a cross-sectional coverage map indicating whether angular portions of a cross-section of a given longitudinal sections of a colon are deemed adequately or inadequately inspected, in accordance with an embodiment of the disclosure.

Turning to FIG. 6, as the endoscopist commences withdrawal through a longitudinal section of the colon, cross-sectional coverage map 620A initially displays 0% inspection coverage. While loitering in and inspecting surface patches of a given longitudinal section, EVA 115 tracks the inspection and begins to highlight cross-sectional coverage map 620B to reflect an estimated inspection coverage. As the endoscopist continues to inspect a given longitudinal section, more of the circle of cross-sectional coverage map 620C is highlighted until all surface patches of the current longitudinal section are deemed inspected, as represented by cross-sectional coverage map 620D showing 100% inspection coverage. As colonoscope 105 is withdrawn to the next longitudinal section, the inspection status is reset to 0% and the process repeats. If colonoscope 105 is withdrawn past a longitudinal section before that section is fully inspected, when the endoscopist returns to the missed longitudinal section for reinspection, cross-sectional coverage map 620E highlights (e.g., colored red) the missed area to quickly guide the endoscopist to the missed location/surface patch (es).

The inspection status may be determined or estimated using a combination or weighting of one or more of the following factors: (a) loitering time of a camera of colonoscope 105 within the given longitudinal section; (b) a determination of whether all surface patches of the colon within the given longitudinal section is observed by the camera (e.g., sweeps within the FOV of the camera for a threshold period of time); (c) a distance between each of the surface patches and the camera when each of the surface patches is observed by the camera; (d) an angle of viewing incidence between the camera and each of the surface patches when each of the surface patches is observed by the camera, or (e) an ML analysis of the colonoscopy video to determine whether any scene potentially included an anatomical fold or area where additional colon anatomy may have be hidden from the FOV. The distance and viewing angles may be thresholded such that surface patches that technically sweep into the FOV of the camera but are either too far away or occur at too steep of an angle may be deemed to not have been adequately observed even though the surface patch did pass within the FOV of the camera. When operating within threshold limits for viewing distance and angle of viewing incidence, loitering times may be adjusted depending upon the actual viewing distance and/or angle of viewing incidence. For example, a viewing distance that does not exceed a threshold maximum may still require twice the loitering time if its distance is considered longer than typical, but does not exceed a maximum distance permitted. Yet another factor that may be considered when determining inspection status is image quality while observing a given surface patch, which may include focus, contrast, sharpness or other image quality characteristics. Again, permissible thresholds may be enforced and loitering multipliers applied for sub-optimal conditions when observing a given surface patch. In some embodiments, any or all of the above factors may be used as ground truth data when training an ML model to estimate or otherwise "deem" an longitudinal section as adequately or inadequately inspected.

In one embodiment, cross-sectional coverage map 220 (or 620A-620D) may visually indicate the angular portions observed/not observed for a given longitudinal section. In this manner, the endoscopist is quickly guided as to which perimeter surface patches still need to be observed for a given depth or longitudinal position. In yet another embodiment, cross-sectional coverage map 220 is merely an overall percentage estimate of the surface patches observed within a longitudinal section without specifically connoting angular directions of observed and unobserved portions.

Returning to FIG. 2, colonoscopy UI 200 includes a region for displaying procedure data 225. The illustrated embodiment of procedure data 225 includes scope information 230, procedure timer 235, withdrawal timer 240, polyp detected status 245, polyp detected history 250, and notifications 255. Scope information 230 may include metadata pertinent to the particular colonoscope 105 such as camera resolution, software/firmware version, frame rate, color space, etc.

Procedure timer(s) 235 may include one or more timers that track the overall procedure time since commencement of the insertion phase, track the procedure time of just the insertion phase, or track the procedure time since commencement of the withdrawal phase. Withdrawal timer 240 displays an estimated withdrawal time to complete the withdrawal phase of the colonoscopy procedure. The estimated withdrawal time may be calculated using a trained neural network upon inspecting the colon during the insertion phase and may further be updated as the withdrawal phase progresses. As such, the estimated withdrawal time may not be displayed until after completion of the insertion phase and represents a sort of countdown timer until completion of the withdrawal phase.

Figure 7:
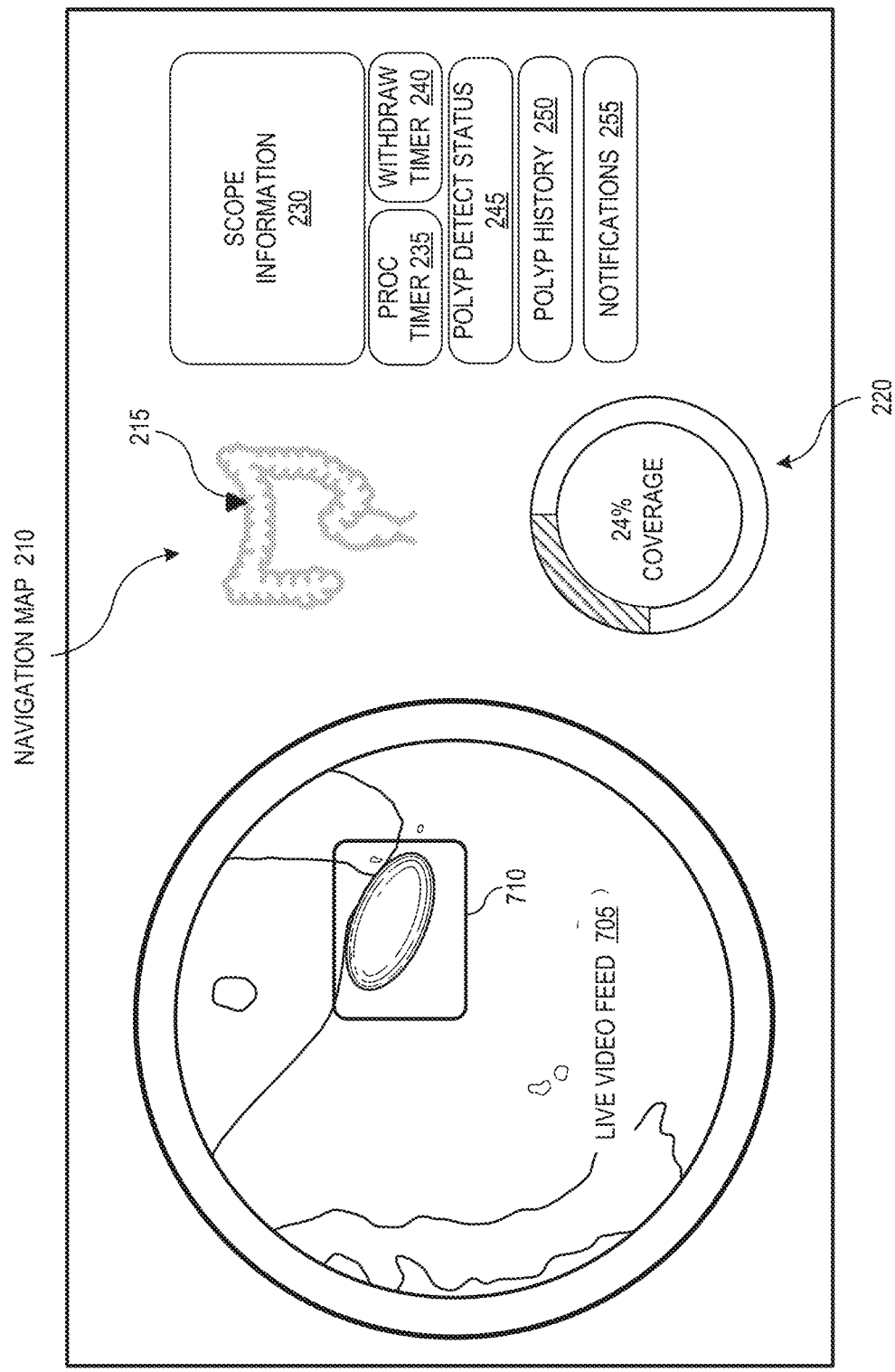
FIG. 7 illustrates how polyps detected within a field of view of the live video stream may be annotated, in accordance with an embodiment of the disclosure.

Polyp detect status 245 represents an indication of whether the image analysis and polyp detect software has detected a polyp in the current FOV or live image feed currently displayed in video region 205. Referring to FIG. 7, if a polyp is detected in live video feed 705, then the detected polyp may be highlighted or accentuated with an annotation 710 clearly identifying its location within the displayed image. Although FIG. 7 illustrates annotation 710 as a box outline, the annotation may be implemented using a variety of different shapes, colors, shadings, labels, etc.

Figures 8A, 8B, 8C:
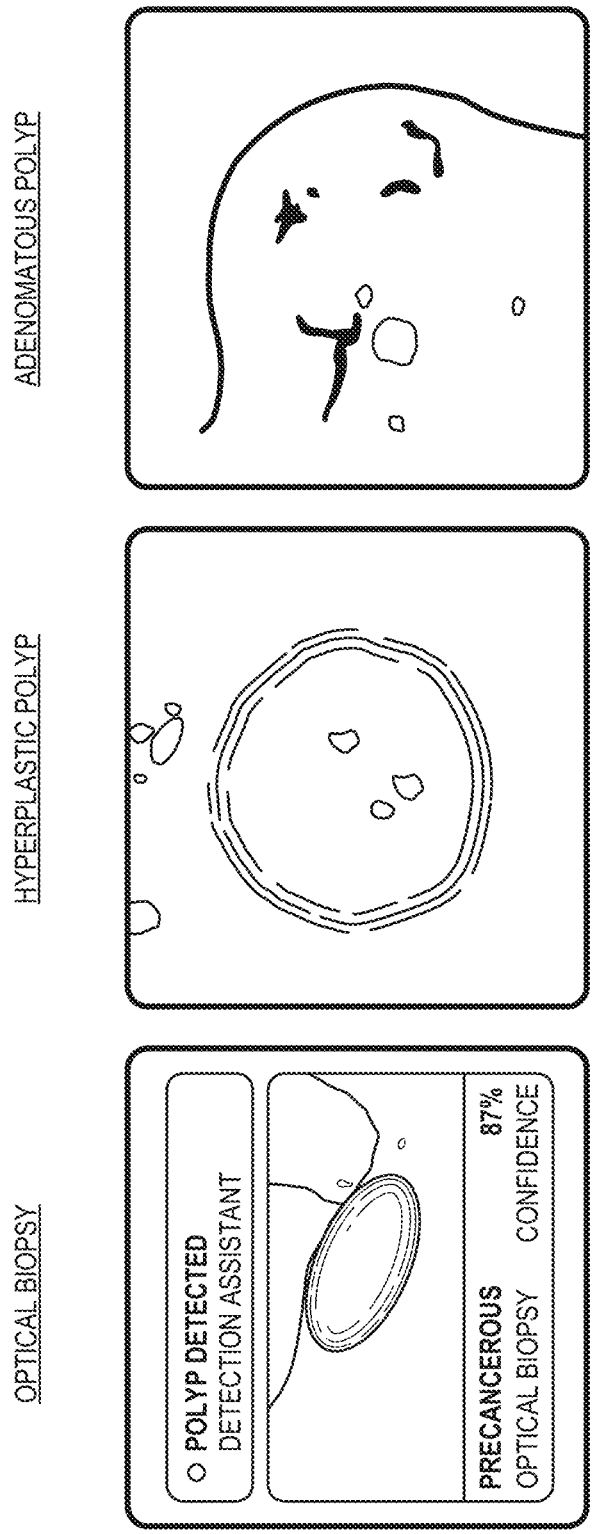
FIGS. 8A, B, and C illustrate reference images of polyps that may be presented on the colonoscopy user-interface based upon an optical biopsy of a detected polyp, in accordance with an embodiment of the disclosure.

Polyp detected history 250 represents a count of the overall number of detected polyps. Additionally, polyp detected history 250 may include a selectable menu for displaying further information regarding the particular detected polyps. For example, if an ML classifier is applied to perform optical biopsies on the detected polyps, then the results of the optical biopsy (see FIG. 8A) may be accessed via the polyp detected history 250 by selecting a given polyp. Alternatively, optical biopsy results and/or reference images for comparison may automatically appear when a polyp is identified in the FOV. The results may include a classification of benign, precancerous, cancerous, etc. along with display of a confidence interval. In yet other embodiments, the classification may include other classifications such as hyperplastic polyp (FIG. 8B), adenomatous polyp (FIG. 8C), etc. Reference images of polyps (FIGS. 8B and 8C) corresponding to the classification of a polyp may be linked and presented upon selection so that the endoscopist may compare the live video feed image against a reference image during real-time observation of a given polyp. Alternatively, FIG. 8B or 8C may represent or include static screen captures of the polyp enabling the endoscopist to more easily inspect the polyp without worrying about moving/controlling the colonoscope to maintain an adequately still image for live inspection. Finally, procedure data 225 may further include a section for notifications 255 where miscellaneous notifications including polyp types/classifications may also be presented.

Embodiments disclosed herein provide a colonoscopy UI 200 that contemporaneously presents the live video feed from colonoscope 105 alongside contextual/orientational data from navigation map 210, cross-sectional coverage map 220, and procedure data 225. These contemporaneous visual aids provide a higher level of context and orientation to the endoscopist, thereby improving the reliability of the colonoscopy procedure and confidence that all polyps are detected.

Figure 9:
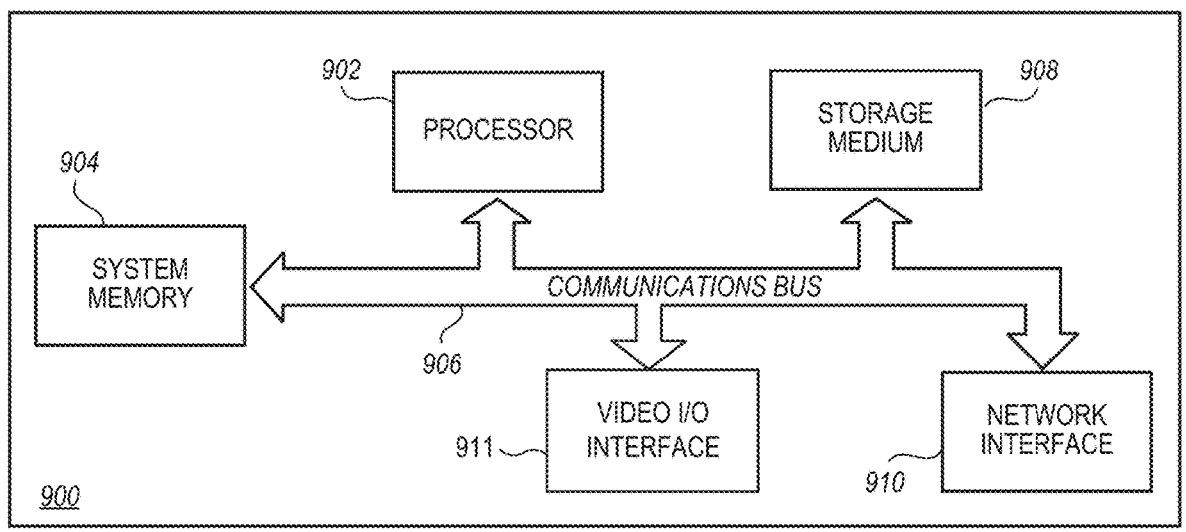
FIG. 9 is a functional block diagram illustrating a demonstrative computing device for implementing an endoscopy video assistant, in accordance with any embodiment of the disclosure.

FIG. 9 is a block diagram that illustrates aspects of a demonstrative computing device appropriate for implementing EVA 115, in accordance with embodiments of the present disclosure. Those of ordinary skill in the art will recognize that computing device 900 may be implemented using currently available computing devices or yet to be developed devices.

In its most basic configuration, computing device 900 includes at least one processor 902 and a system memory 904 connected by a communication bus 906. Depending on the exact configuration and type of device, system memory 904 may be volatile or nonvolatile memory, such as read only memory ("ROM"), random access memory ("RAM"), EEPROM, flash memory, or similar memory technology. Those of ordinary skill in the art will recognize that system memory 904 typically stores data and/or program modules that are immediately accessible to and/or currently being operated on by the processor 902. In this regard, the processor 902 may serve as a computational center of computing device 900 by supporting the execution of instructions.

As further illustrated in FIG. 9, computing device 900 may include a network interface 910 comprising one or more components for communicating with other devices over a network. Embodiments of the present disclosure may access basic services that utilize network interface 910 to perform communications using common network protocols. Network interface 910 may also include a wireless network interface configured to communicate via one or more wireless communication protocols, such as WiFi, 2G, 3G, 4G, LTE, WiMAX, Bluetooth, and/or the like.

In the exemplary embodiment depicted in FIG. 9, computing device 900 also includes a storage medium 908. However, services may be accessed using a computing device that does not include means for persisting data to a local storage medium. Therefore, the storage medium 908 may be omitted. In any event, the storage medium 908 may be volatile or nonvolatile, removable or nonremovable, implemented using any technology capable of storing information such as, but not limited to, a hard drive, solid state drive, CD-ROM, DVD, or other disk storage, magnetic cassettes, magnetic tape, magnetic disk storage, and/or the like.

The illustrated embodiment of computing device 900 further includes a video input/out interface 911. Video I/O interface 911 may include an analog video input (e.g., composite video, component video, VGG connector, etc) or a digital video input (e.g., HDMI, DVI, DisplayPort, USB-A, USB-C, etc.) to receive the live video feed from colonoscope 105 and a similar type of video output port to output the live video feed within colonoscopy UI 200 to display 110. In one embodiment, video I/O interface 911 may also represent a graphics processing unit capable of performing the necessary computational video processing to generate and render colonoscopy UI 200.

As used herein, the term "computer-readable medium" includes volatile and non-volatile and removable and non-removable media implemented in any method or technology capable of storing information, such as computer-readable instructions, data structures, program modules, or other data. In this regard, the system memory 904 and storage medium 908 depicted in FIG. 9 are merely examples of computer-readable media.

Suitable implementations of computing devices that include a processor 902, system memory 904, communication bus 906, storage medium 908, and network interface 910 are known and commercially available. For ease of illustration and because it is not important for an understanding of the claimed subject matter, FIG. 9 does not show some of the typical components of many computing devices. In this regard, the computing device 900 may include input devices, such as a keyboard, keypad, mouse, microphone, touch input device, touch screen, tablet, and/or the like. Such input devices may be coupled to computing device 900 by wired or wireless connections including RF, infrared, serial, parallel, Bluetooth, USB, or other suitable connection protocols using wireless or physical connections. Since these devices are well known in the art, they are not illustrated or described further herein.

The above user-interface has been described in terms of a colonoscopy and is particularly well-suited as a colonoscopy user-interface to aid visualization of colonoscopy procedures. However, it should be appreciated that user-interface 200 may be more broadly/generically described as an endoscopy user-interface that may be used to visualize endoscopy procedures, in general, related to other anatomical structures. For example, the user-interface is applicable to aid visualization of other gastroenterological procedures including endoscopy procedures within the upper and lower gastrointestinal tracts. In yet other examples, the user-interface may be used to visualize exploratory endoscopy procedures of non-gastroenterological structures such as the esophagus, bronchial tubes, other tube-like anatomical structures, etc. When adapting the user-interface to visualize other endoscopy procedures, navigational map 210 would represent a map of the corresponding anatomical structure being explored and cross-sectional coverage map 220 would represent cross-sectional or perimeter inspection coverage of the corresponding anatomical structure. Similarly, coverage map 505 illustrated in FIG. 5 could be adapted to represent inspection coverage of a variety of different anatomical structures and the optical biopsy images and reference images illustrated in FIGS. 8A—8C may be adapted for various types of anatomical structures, tissue types, tumors, etc. to support clinical workflow related to other endoscopy procedures.

The processes and user-interface described above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, some of the processes or logic for implementing the user-interface may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one machine-accessible storage medium that provides instructions that, when executed by a machine, will cause the machine to perform operations comprising:
    generating a colonoscopy user-interface for display on a screen;
    outputting a live video feed received from a colonoscope for display within a video region of the colonoscopy user-interface;
    generating a navigational map that depicts longitudinal sections of a colon for display within the colonoscopy user-interface;
    annotating one of the longitudinal sections on the navigational map to visually indicate an inspection status of the one of the longitudinal sections, wherein the inspection status indicates whether the one of the longitudinal sections is deemed adequately or inadequately inspected by the colonoscope; and
    determining the inspection status based upon at least a loitering time of a camera of the colonoscope in the one of the longitudinal sections.

2. The at least one machine-accessible storage medium of claim 1, wherein the live video feed and the navigational map are both contemporaneously presented within the colonoscopy user-interface.

3. The at least one machine-accessible storage medium of claim 1, wherein the annotating is updated during a withdrawal phase of a colonoscopy procedure.

4. The at least one machine-accessible storage medium of claim 1, further providing instructions that, when executed by the machine, will cause the machine to perform further operations, comprising:
    moving a position marker along the navigational map as the colonoscope moves within the colon, wherein the position marker indicates a real-time position of a field of view of the live video feed acquired by the colonoscope within the colon.

5. The at least one machine-accessible storage medium of claim 4, further providing instructions that, when executed by the machine, will cause the machine to perform further operations, comprising:
    annotating each of the longitudinal sections with a corresponding inspection status as the position marker passes through a corresponding one of the longitudinal sections while the colonoscope is withdrawn from the colon.

6. The at least one machine-accessible storage medium of claim 1, wherein presenting the navigational map further comprises:
    either, initially presenting the navigational map or transitioning the navigational map from a first shade to a second shade, once a distal tip of the colonoscope reaches a cecum of the colon at an end of an insertion phase of a colonoscopy procedure.

7. The at least one machine-accessible storage medium of claim 1, wherein determining the inspection status is further based upon at least one of:
- a determination of whether all surface patches of the colon within the one of the longitudinal sections is observed by the camera;
- a distance between each of the surface patches and the camera when each of the surface patches is observed by the camera; or
- an angle of viewing incidence between the camera and each of the surface patches when each of the surface patches is observed by the camera.

8. The at least one machine-accessible storage medium of claim 1, wherein the navigational map is an anatomical atlas representative of the colon.

9. The at least one machine-accessible storage medium of claim 1, wherein the navigational map comprises a 3D model of the colon constructed during an insertion phase of a colonoscopy procedure.

10. The at least one machine-accessible storage medium of claim 1, further providing instructions that, when executed by the machine, will cause the machine to perform further operations, comprising:
- presenting a cross-sectional coverage map indicating whether angular portions of a cross-section of the one of the longitudinal sections of the colon are deemed adequately or inadequately inspected by the colonoscope.

11. The at least one machine-accessible storage medium of claim 1, further providing instructions that, when executed by the machine, will cause the machine to perform further operations, comprising:
- displaying an estimated withdrawal time to complete a withdrawal phase of a colonoscopy procedure; and
- updating the estimated withdrawal time during the withdrawal phase.

12. The at least one machine-accessible storage medium of claim 1, further providing instructions that, when executed by the machine, will cause the machine to perform further operations, comprising:
- overlaying a guidance arrow on the live video feed guiding an operator of the colonoscope back to the one of the longitudinal sections when the colonoscope has been withdrawn past the one of the longitudinal sections that is deemed inadequately inspected.

13. The at least one machine-accessible storage medium of claim 1, further providing instructions that, when executed by the machine, will cause the machine to perform further operations, comprising:
- collecting coverage data from a multitude of colonoscopy procedures indicating colon portions most likely to be inadequately observed during the multitude of colonoscopy procedures.

14. The at least one machine-accessible storage medium of claim 1, further providing instructions that, when executed by the machine, will cause the machine to perform further operations, comprising:
- annotating a detected polyp in the live video feed.

15. The at least one machine-accessible storage medium of claim 14, further providing instructions that, when executed by the machine, will cause the machine to perform further operations, comprising:
- classifying the detected polyp based upon image analysis of the detected polyp; and
- presenting, within the colonoscopy user-interface, one or more reference images of polyps based upon the classifying for visual comparison against the detected polyp currently displayed in the live video feed.

16. At least one machine-accessible storage medium that provides instructions that, when executed by a machine, will cause the machine to output a signal for rendering a user-interface to a display, the user-interface adapted for visualizing an endoscopy procedure, the user-interface comprising:
- a video region in which a live video feed received from an endoscope is displayed;
- a navigational map that depicts longitudinal sections of an anatomical structure;
- one or more coverage annotations presented on the navigation map that indicate whether one or more of the longitudinal sections is deemed adequately inspected or inadequately inspected during the endoscopy procedure; and
- a cross-sectional coverage map indicating an estimated inspection coverage of a given longitudinal section of the anatomical structure, wherein the estimated inspection coverage for the given longitudinal section increases as a camera of the endoscope loiters within the given longitudinal section inspecting different angular portions of the given longitudinal section.

17. The least one machine-accessible storage medium of claim 16, wherein the user-interface further comprises:
- a position marker displayed on the navigational map indicating a real-time position of a field of view of the live video feed acquired by the endoscope within the anatomical structure, wherein the position marker moves along the navigation map as the endoscope moves within the anatomical structure.

18. The least one machine-accessible storage medium of claim 16, wherein the cross-sectional coverage map indicates which angular portions of the given longitudinal section of the anatomical structure are deemed adequately inspected or inadequately inspected by the endoscope.

19. The least one machine-accessible storage medium of claim 16, wherein the user-interface comprises a colonoscopy user-interface, the endoscopy procedure comprises a colonoscopy procedure, the endoscope comprises a colonoscope, and the anatomical structure comprises a colon.

20. The least one machine-accessible storage medium of claim 19, wherein the colonoscopy user-interface further comprises:
- a guidance arrow overlaying the live video feed and guiding an operator of the colonoscope back to one of the longitudinal sections when the colonoscope has been withdrawn past the one of the longitudinal sections that is deemed inadequately inspected during a withdrawal phase of the colonoscopy procedure.

21. The least one machine-accessible storage medium of claim 19, wherein the colonoscopy user-interface further comprises one or more of:
- a withdrawal timer displaying an estimated withdrawal time to complete a withdrawal phase of the colonoscopy procedure;
- a polyp detected status region that displays an indication whether a polyp is detected within a current field of view of the live video field;
- a polyp detected history region that displays a history of polyps detected during the colonoscopy procedure; or
- a notification region that displays a notification when a surface patch of the colon is deemed inadequately inspected after a camera of the colonoscope is withdrawn past the surface patch during a withdrawal phase of the colonoscopy procedure.

22. At least one machine-accessible storage medium that provides instructions that, when executed by a machine, will cause the machine to perform operations comprising:
- generating a colonoscopy user-interface for display on a screen;
- outputting a live video feed received from a colonoscope for display within a video region of the colonoscopy user-interface;
- generating a navigational map that depicts longitudinal sections of a colon for display within the colonoscopy user-interface;
- annotating one of the longitudinal sections on the navigational map to visually indicate an inspection status of the one of the longitudinal sections, wherein the inspection status indicates whether the one of the longitudinal sections is deemed adequately or inadequately inspected by the colonoscope; and
- generating a cross-sectional coverage map for display within the colonoscopy user-interface, wherein the cross-sectional coverage map indicates an estimated inspection coverage of a given longitudinal section of the colon and further indicates which angular portions of the given longitudinal section of the colon are deemed adequately inspected or inadequately inspected.

\* \* \* \* \*